(12) United States Patent
Sambusseti et al.

(10) Patent No.: US 9,750,597 B2
(45) Date of Patent: Sep. 5, 2017

(54) ORTHOTOPIC ARTIFICIAL BLADDER ENDOPROSTHESIS

(71) Applicants: Antonio Sambusseti, Cremona (IT); Gianni Cancarini, Brescia (IT)

(72) Inventors: Antonio Sambusseti, Cremona (IT); Gianni Cancarini, Brescia (IT)

(*) Notice: Subject to any disclaimer, the term of this patent is extended or adjusted under 35 U.S.C. 154(b) by 88 days.

(21) Appl. No.: 14/428,107

(22) PCT Filed: Oct. 10, 2013

(86) PCT No.: PCT/IB2013/059254
§ 371 (c)(1),
(2) Date: Mar. 13, 2015

(87) PCT Pub. No.: WO2014/060911
PCT Pub. Date: Apr. 24, 2014

(65) Prior Publication Data
US 2015/0223924 A1   Aug. 13, 2015

(30) Foreign Application Priority Data

Oct. 16, 2012 (IT) .............................. MI2012A1743

(51) Int. Cl.
*A61F 2/04* (2013.01)
(52) U.S. Cl.
CPC ................ *A61F 2/042* (2013.01); *A61F 2/04* (2013.01); *A61F 2250/003* (2013.01)
(58) Field of Classification Search
CPC ........... A61F 2/04; A61F 2/042; A61F 2/0063
See application file for complete search history.

(56) References Cited

U.S. PATENT DOCUMENTS

| 9,375,306 B2 | 6/2016 | Sambusseti |
| 2002/0007223 A1 | 1/2002 | Matapurkar |
| 2007/0276507 A1* | 11/2007 | Bertram ................. A61F 2/042 623/23.65 |
| 2008/0319460 A1 | 12/2008 | Cortellini |
| 2011/0270409 A1 | 11/2011 | Sambusseti |
| 2013/0103164 A1 | 4/2013 | Sambusseti |

(Continued)

FOREIGN PATENT DOCUMENTS

| CN | 101304706 A | 11/2008 |
| CN | 102271621 A | 12/2011 |
| FR | 2116838 A5 | 7/1972 |

(Continued)

OTHER PUBLICATIONS

Office Action dated Nov. 17, 2015 from Chinese Patent Application No. 201380048618.9 to Sambusseti et al.

(Continued)

*Primary Examiner* — Katrina Stransky
*Assistant Examiner* — Daniel Bissing
(74) *Attorney, Agent, or Firm* — Vorys, Sater, Seymour and Pease LLP

(57) ABSTRACT

An orthotopic artificial bladder endoprosthesis includes two portions connected to each other; each portion including a respective resorbable cap made of a PGA fiber fabric and a respective frame, associated with the cap, obtained by means of PGA/PLA copolymer; the portions being connected together in order to define a closed enclosure.

19 Claims, 3 Drawing Sheets

(56) References Cited

U.S. PATENT DOCUMENTS

2015/0045907 A1     2/2015   Sambusseti
2016/0000552 A1     1/2016   Sambusseti et al.

FOREIGN PATENT DOCUMENTS

| IT | WO 2011064110 A1 * | 6/2011 | ............ A61F 2/042 |
| WO | 2007039159 A1 | 4/2007 | |
| WO | 2007095193 A2 | 8/2007 | |
| WO | 2009077047 A1 | 6/2009 | |
| WO | 2011018300 A1 | 2/2011 | |
| WO | 2011064110 A1 | 6/2011 | |
| WO | 2011112626 A1 | 9/2011 | |
| WO | 2011137394 A1 | 11/2011 | |
| WO | 2011138371 A1 | 11/2011 | |
| WO | 2011160875 A1 | 12/2011 | |
| WO | 2013135543 A1 | 9/2013 | |

OTHER PUBLICATIONS

International Search Report and Written Opinion dated Feb. 13, 2014 for PCT/IB2013/059254 to Antonio Sambusseti et al. filed Oct. 10, 2013.
Dec. 9, 2015, Office Action for U.S. Appl. No. 14/427,968, Antonio Sambusseti et al., filed Mar. 13, 2015.

* cited by examiner

ORTHOTOPIC ARTIFICIAL BLADDER ENDOPROSTHESIS

CROSS-REFERENCE TO RELATED APPLICATIONS

This is a §371 National Stage Application of International Application No. PCT/IB2013/059254 filed on Oct. 10, 2013, claiming the priority of Italian Patent Application No. MI2012A001743 filed on Oct. 16, 2012.

The present invention relates to an orthotopic artificial bladder endoprosthesis.

The application of the present invention lies in the replacement of the bladder of a patient, if the latter is suffering from serious incurable diseases such to compromise the correct function thereof.

Known bladder endoprostheses comprise a balloon casing made with an impermeable layered silicone membrane.

Such casing is sufficiently rigid so as to stably keep its shape and flexible to be able to be manually compressed to ensure that it empties.

The casing has a connection element located at a lower portion of the casing to connect with the patient's urethra. Similarly, two connection bodies are located at the top to enable connection with the ureters.

These connections are achieved by suturing or by simply interlocking.

Following the implant of the endoprosthesis in the patient, there is the formation of a musculo-fibrous tissue layer (not impermeable) around the casing. In such a manner, a neo-bladder is generated around the endoprosthesis.

Since the endoprotheses of known type are permanent, complications can occur even after the complete rehabilitation of the patient.

Indeed, it may occur that an infection hits the neobladder in an accidental manner or following the use of catheters.

In such case, a suitable antibiotic treatment is necessary. Such drugs are effective in extinguishing the bacterial loads nested in biological tissue and have poor or even zero effect on bacterial loads nested on artificial materials like those that make up the casing. Disadvantageously, therefore, endoprostheses of known type can represent an obstacle to the effectiveness of antibiotic treatments.

In this context, the technical task underlying the present invention is to propose an orthotopic artificial bladder endoprosthesis that overcomes the drawback of the abovementioned prior art.

In particular, the object of the present invention is to provide an orthotopic artificial bladder endoprosthesis that limits the risks associated with bacterial infections.

The specified technical task and the specified object are substantially achieved by an orthotopic artificial bladder endoprosthesis comprising the technical characteristics set forth in one or more of the enclosed claims.

Further characteristics and advantages of the present invention will emerge more clearly from the following non-limiting description of a preferred but not exclusive embodiment of an orthotopic artificial bladder endoprosthesis, as illustrated in the enclosed drawings in which.

Figure 1:
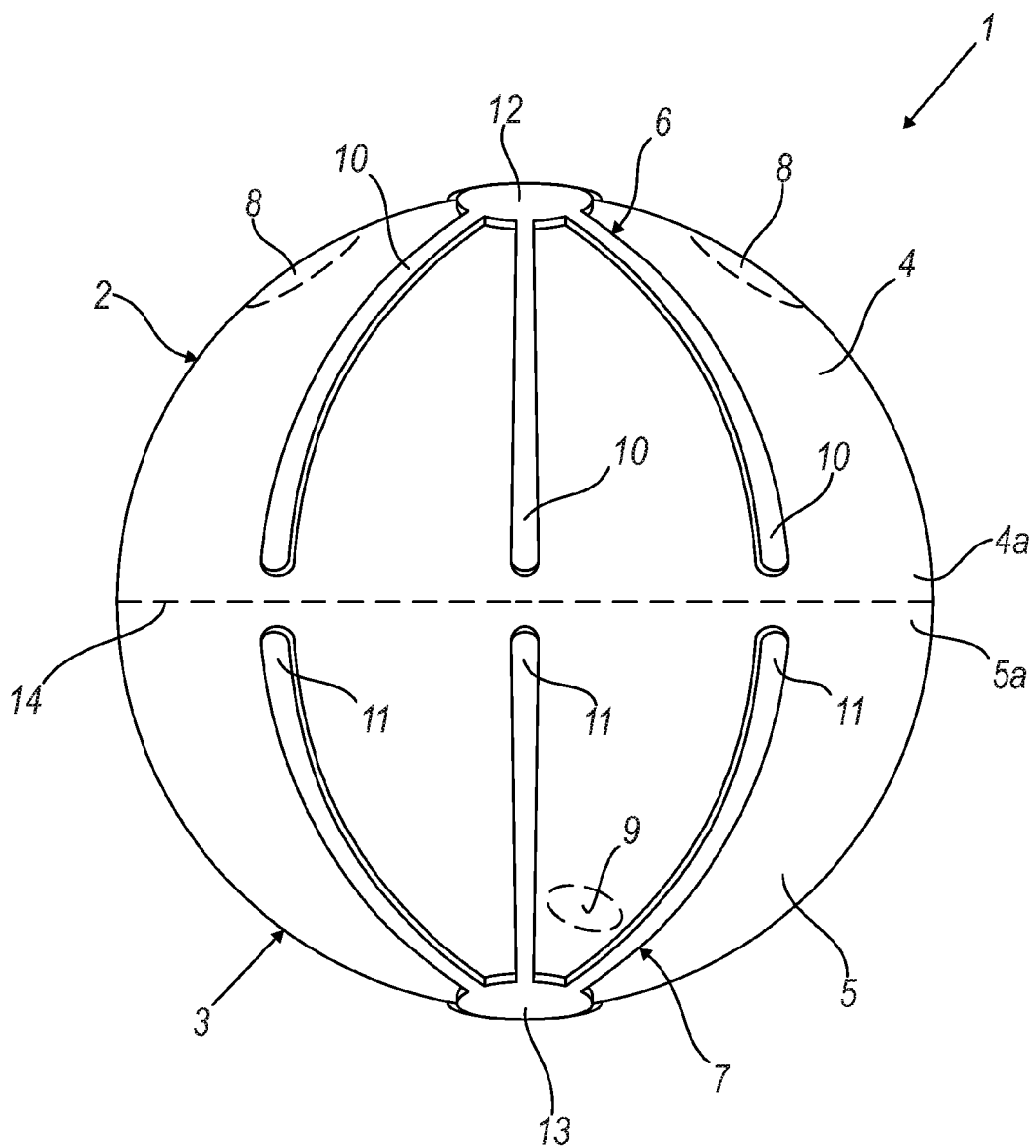
FIG. 1 is a schematic side view of an orthotopic artificial bladder endoprosthesis in accordance with the present invention according to a first embodiment.

With reference to the enclosed figures, reference number indicates an orthotopic artificial bladder endoprosthesis in accordance with the present invention. The endoprosthesis 1 comprises two portions 2,3 that are coupled together. Preferably, the portions 2,3 are equivalent to each other. Preferably, the portions 2,3 are connected to each other by means of resorbable suture.

The portions 2,3 have substantially semispherical form and are coupled in a manner such that their concavities are mutually facing. In such a manner, the two coupled portions 2,3 define a closed enclosure for containing the urine. The enclosure has a volume substantially comprised between 100 cm$^3$ and 900 cm$^3$, preferably being 400 cm$^3$.

A first portion 2 is intended to be connected to ureters of a patient. A second portion 3 is intended to be connected to a urethra of the patent.

Each portion 2,3 comprises a resorbable cap 4,5. The caps 4,5 are connected to each other.

In particular, the cap 4 of the first portion 2 and the cap 5 of the second portion 3 are connected to each other along the respective edges 4a,5b.

The connection between the caps 4,5 is obtained by means of a resorbable suture 14.

Figure 3:
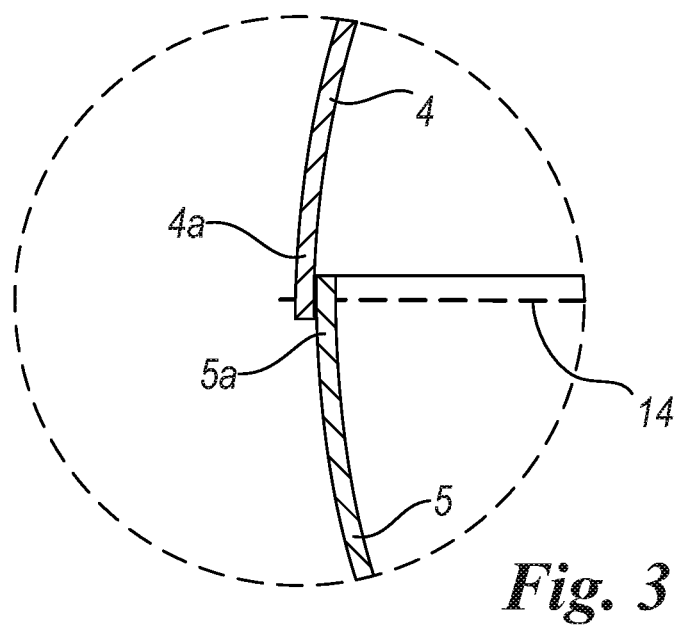
FIGS. 3 and 4 are cross-section views of respective embodiments of a detail of the endoprosthesis of FIG. 1.

In accordance with the embodiment illustrated in FIG. 3, the coupling is carried out by fitting an internal side of the edge 4a of the cap 4 of the first portion 2 with an external side of the edge 5a of the cap 5 of the second portion 3.

In accordance with the non-illustrated embodiment, the coupling is carried out by fitting an external side of the edge 4a of the cap 4 of the first portion 2 with an internal side of the edge 5a of the cap 5 of the second portion 3.

Figure 4:
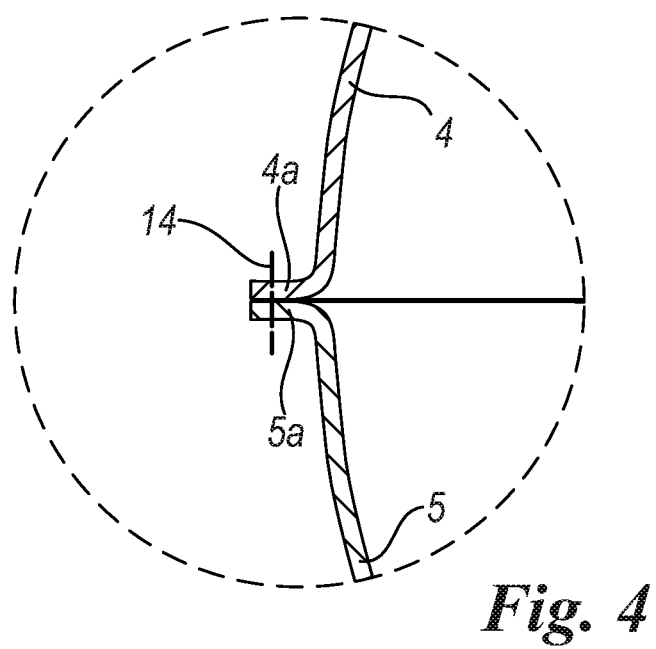

In accordance with the embodiment illustrated in FIG. 4, the coupling is carried out by fitting an internal side of the edge 4a of the cap 4 of the first portion 2 with an internal side of the edge 5a of the cap 5 of the second portion 3.

Each cap 4,5 is obtained with a fabric with substantially circular, flat form. In addition, each portion 2,3 comprises frame 6,7 fixed to the fabric.

The frame 6,7 acts as a load-bearing structure for the fabric, allowing it to assume a dome-shaped form which is maintained as such even under the weight of the growth of the fibrous capsule.

The fabric of the caps 3,4 is made using an ultra-light thread or monofilament deriving from preferably homopolymer PGA (polyglycolide or poylglycolic acid) fibers. PGA is a highly biocompatible and resorbable polymer and resistant to urine. Specifically, the resorption time of PGA is approximately one month.

Advantageously, the use of PGA fibers in obtaining the fabric of the caps 3,4 allows the formation of the musculo-fibrous tissue during the resorption phase of the endoprosthesis 1.

In addition, always during resorption, there is the formation of a transition epithelium layer, which is also called urothelium. Advantageously, the layer of urothelium is impermeable, an essential fact to ensure the correct functioning of the prosthesis and the neobladder that is being formed.

Furthermore, once the endoprosthesis 1 is inserted, the fabric of the caps 4,5 the coating is impregnated with blood and in particular with plasma, which allows the antibiotic drugs to be effective on the endoprosthesis.

The fabric of the caps 3,4 can be obtained by weaving the PGA thread in various ways, giving rise to a knitted fabric, a woven fabric or a non-woven fabric.

Preferably, the fabric is a knitted fabric, still more preferably a warp knitted fabric.

In this case, the fabric has a rougher surface capable of assuming a net configuration with sufficiently small meshes.

In detail, its weft is such that its interstitial space is less than 200 μm, preferably around 160 μm, corresponding to an average area of the holes equal to approximately 0.02 mm². This ensures impermeability to urine, preventing leaks.

Furthermore, the fabric is preferably textured so as to give it even greater surface roughness and greater rigidity and impermeability. The greater roughness of the fabric limits the risk of adhesion of the fibrous capsule.

Purely by way of example, the fabric has a diameter substantially comprised between 8 cm and 20 cm.

Still by way of example, the fabric has a thickness substantially comprised between 0.3 mm and 0.6 mm, more preferably comprised between 0.4 mm and 0.53 mm, still more preferably being substantially 0.45 mm.

On the fabric of the cap 4 of the first portion 2, there are two connection areas 8 designed to connect the ureters of the patient to the endoprosthesis 1. In particular, when the endoprosthesis 1 is implanted, the surgeon makes a hole in the cap 4 at the connection areas 8 to suit the diameter of the ureters, flares the free ends of the ureters and sutures such ends to the cap 4. Analogously, on the fabric of the cap 5 of the second portion 3, a connection area 9 is present designed to connect the urethra of the patient to the endoprosthesis 1. In particular, when the endoprosthesis 1 is implanted, the surgeon makes a hole in the cap 5 at the connection area 9 to suite the diameter of the urethra, flares the free end of the urethra and sutures such end to the cap 5.

Each of the frames 6,7 comprises a plurality of arms 10,11 arranged as a star and defining a dome profile. More in detail, the arms 10,11 all have a curved shape and are fixed together at a joining portion 12,13 located at the top of each portion 2,3.

The frames 6,7 are arranged outside the caps 4,5. In particular, each frame 6,7 is fixed to the fabric by means of resorbable sutures.

Generally, the thickness of the frames 6,7, i.e. the arms 10,11 and the joining portions 12,13, is comprised between 0.1 mm and 10 mm, preferably between 0.5 mm and 2 mm. In a preferred embodiment, the thickness is substantially 1 mm.

The frames 6,7 are obtained by injection of a copolymer of lactic acid and glycolic acid, indicated as PGA/PLA (poly(lactic-co-glycolic) acid) whose domed shape is imparted when hot by means of thermoforming.

Since lactic acid is a chiral molecule, different types of polymer, PDLA, PLLA, PDLLA exist, where D and L represent the two stereoisomers. PLLA has a crystallinity of 37%, a vitreous transition temperature of between 50° C. and 80° C. and a melting temperature of between 173° C. and 178° C., whereas polymer deriving from the polymerization of a racemic mixture, PDLLA, is amorphous.

The term poly(lactic) acid is here intended to identify all of the various above-mentioned types of PLA.

The PGA/PLA copolymer, with which the frame 9 is made, is formed by a quantity of PGA comprised between 20% and 30% and by a quantity of PLA correspondingly comprised between 70% and 80%.

Particularly preferred as a PGA/PLA (poly(lactic-co-glycolic) acid) copolymer is the copolymer poly(L-lactic-co-glycolic) (PLLA/PGA) in which the L-lactic acid has a molar percent of 82-88% in moles whereas glycolic acid has a molar percent of 18-12%. This copolymer is commercially known by the name of Resomer® LG855S.

According to that illustrated in FIG. 1, the arms 10 of the first portion 2 and the arms 11 of the second portion 3 are distinct and spaced.

The free ends of the arms 10 of the first portion 2 and of the arms 11 of the second portion 3 are aligned with each other.

In a non-illustrated embodiment, the free ends of the arms 10 of the first portion 2 and of the arms 11 of the second portion 3 are offset from each other and alternated.

Figure 2:
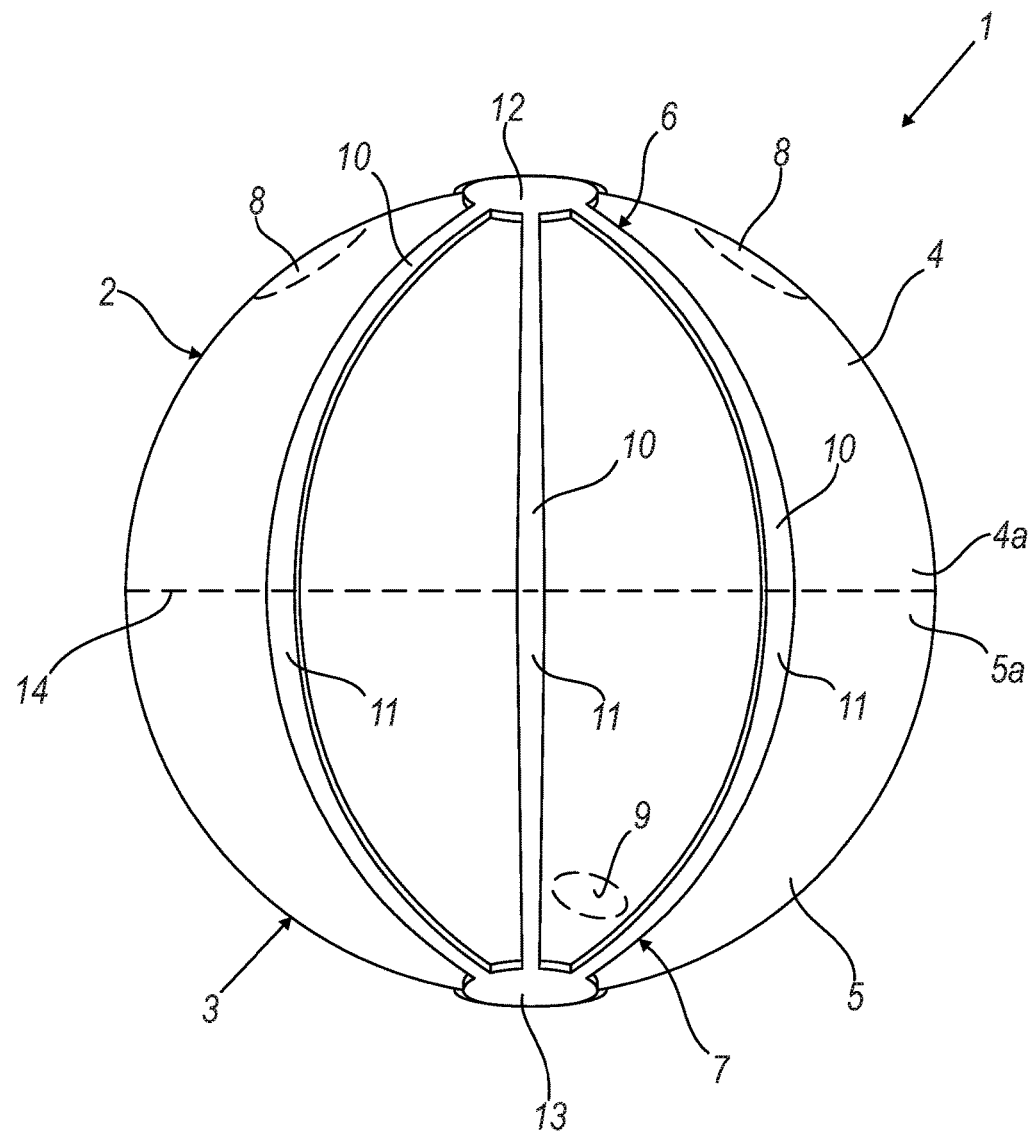
FIG. 2 is a schematic side view of the orthotopic artificial bladder endoprosthesis in accordance with the present invention according to a second embodiment.

According to that illustrated in FIG. 2, the arms 10 of the first portion 2 and the arms 11 of the second portion 3 are made in a single piece in order to give further rigidity to the endoprosthesis 1.

The Applicant has surprisingly found that the caps 4,5 made with the PGA fabric as described above, in particular textured, in combination with the PGA/PLA frames 6,7, show a good mechanical consistency and sufficient rigidity, even in the presence of urine, and so are capable of ensuring a correct deformation of the bladder during emptying and/or filling thereof, at the same time showing a good resistance to leaks of urine.

Furthermore, the caps 4,5 and the frames 6,7 have proven to be neutral when in contact with growing neotissue. This involves a rapid population of the device by the cells of the surrounding growing tissue. At the same time, adhesion has proven to be reduced due to the reduced interaction between the polymers that comprise the caps 4,5 and the frames 6,7 and the biological molecules, thus ensuring a fusion with the patient's internal tissues.

The invention described reaches the pre-established object.

Indeed, since the endoprosthesis is completely soaked with blood and plasma once inserted in the patient, the antibiotic drugs are fully effective and the risk of complications due to bacterial infections is considerably reduced.

In addition, it should be observed that the endoprosthesis, object of the present invention, is completely resorbable. In such a manner, no foreign body remains in the patient after the operation.

The invention claimed is:

1. An orthotopic artificial bladder endoprosthesis comprising two portions connected to each other;
   each portion comprising a respective resorbable cap made of a PGA fiber fabric and a respective frame associated with said resorbable cap, each frame being made of a PGA/PLA copolymer and comprising a plurality of curved arms arranged as a star and defining a dome-like profile,
   wherein each frame is a load-bearing structure for the PGA fiber fabric of each portion to respectively assume the dome-like profile and each frame has a rigidity for maintaining the PGA fiber fabric of each portion respectively in the dome-like profile;
   said two portions being connected together to define a closed enclosure.

2. The endoprosthesis according to claim 1, wherein said two portions are connected together by resorbable suture.

3. The endoprosthesis according to claim 1, wherein said resorbable caps are mutually connected at their edges.

4. The endoprosthesis according to claim 1, wherein the curved arms of a first portion are fixed to the curved arms of a second portion.

5. The endoprosthesis according to claim 1, wherein the curved arms of a first portion are separated from the curved arms of a second portion.

6. The endoprosthesis according to claim 1, wherein the PGA fiber fabric of said resorbable caps is warp knitted fabric.

7. The endoprosthesis according to claim 1, wherein the PGA/PLA copolymer consists of 30% PGA and 70% PLA.

8. The endoprosthesis according to claim 1, wherein a thickness of the PGA fiber fabric is between 0.1 mm and 2 mm.

9. The endoprosthesis according to claim 1, wherein the PGA fiber fabric is obtained with a thread having a density between 50 and 200 denier.

10. The endoprosthesis according to claim 1, wherein the PGA fiber fabric of said resorbable caps is textured fabric.

11. The endoprosthesis according to claim 1, wherein a thickness of the PGA fiber fabric is between 0.3 mm and 0.6 mm.

12. The endoprosthesis according to claim 1, wherein a thickness of the PGA fiber fabric is between 0.4 mm and 0.53 mm.

13. The endoprosthesis according to claim 1, wherein a thickness of the PGA fiber fabric is 0.45 mm.

14. The endoprosthesis according to claim 11, wherein a thickness of the plurality of curved arms of each frame is between 0.5 mm and 2 mm.

15. The endoprosthesis according to claim 1,
wherein the PGA fiber fabric of each resorbable cap is flexible,
wherein each frame has the rigidity to maintain the PGA fiber fabric in the dome-like profile even under weight of growth of a musculo-fibrous capsule about the orthotopic artificial bladder endoprosthesis, and
wherein the frames are obtained by injection of the PGA/PLA copolymer whose domed shape is imparted by thermoforming.

16. The endoprosthesis according to claim 1, wherein each frame is the load-bearing structure for the PGA fiber fabric, each cap is obtained from PGA fiber fabric with substantially circular flat form prior to being associated with the respective said frame and each frame has a self-supporting said domed shape.

17. The endoprosthesis according to claim 1, wherein each of the curved arms of the first portion is aligned with a respective said curved arm of the second portion.

18. The endoprosthesis according to claim 1, wherein each frame associated with the resorbable cap comprises the plurality of curved arms arranged as a star to define the dome-like profile and arranged outside the resorbable cap.

19. The endoprosthesis according to claim 1, wherein each frame is sufficiently rigid to have a self-supporting dome-like profile.

* * * * *